(12) United States Patent
Suwito

(10) Patent No.: US 11,708,923 B2
(45) Date of Patent: Jul. 25, 2023

(54) TUBING RETENTION DEVICE

(71) Applicant: CareFusion 303, Inc., San Diego, CA (US)

(72) Inventor: Wantjinarjo Suwito, West Linn, OR (US)

(73) Assignee: CAREFUSION 303, INC., San Diego, CA (US)

( * ) Notice: Subject to any disclaimer, the term of this patent is extended or adjusted under 35 U.S.C. 154(b) by 204 days.

(21) Appl. No.: 17/009,572

(22) Filed: Sep. 1, 2020

(65) Prior Publication Data
US 2022/0065373 A1 Mar. 3, 2022

(51) Int. Cl.
*F16L 33/207* (2006.01)
*A61M 39/10* (2006.01)

(52) U.S. Cl.
CPC ......... *F16L 33/2071* (2013.01); *A61M 39/10* (2013.01)

(58) Field of Classification Search
CPC ..... F16L 33/20; F16L 33/207; F16L 33/2071; F16L 33/2075; F16L 33/34
USPC ................................................ 285/244, 21.2
See application file for complete search history.

(56) References Cited

U.S. PATENT DOCUMENTS

| | | | | |
|---|---|---|---|---|
| 1,004,678 A | * | 10/1911 | Nicholls | F16L 21/005 285/244 |
| 1,748,774 A | * | 2/1930 | Kellogg | A47K 7/028 285/244 |
| 3,729,027 A | * | 4/1973 | Bare | F16L 33/03 285/244 |
| 4,313,629 A | * | 2/1982 | Winterhalter | F16L 33/2071 285/242 |
| 4,425,682 A | | 1/1984 | Hashimoto et al. | |
| 4,640,535 A | * | 2/1987 | Hermann | F16L 37/084 285/244 |
| 4,687,234 A | * | 8/1987 | Weinhold | F16L 33/12 285/244 |
| 5,286,068 A | * | 2/1994 | Wiebe | F16L 33/24 285/281 |
| 6,231,085 B1 | | 5/2001 | Olson | |
| 6,779,269 B2 | * | 8/2004 | Green | F16L 33/228 29/890.044 |

(Continued)

OTHER PUBLICATIONS

International Search Report and Written Opinion for Application No. PCT/US2021/048071, dated Dec. 8, 2021, 14 pages.

*Primary Examiner* — David Bochna
(74) *Attorney, Agent, or Firm* — Morgan Lewis & Bockius LLP

(57) ABSTRACT

Tubing retention systems are described herein. A tubing retention system includes a spigot, a tubing, and a collar. The spigot includes a spigot body and a spigot extension extending from the spigot body, wherein the spigot extension comprises a flared portion opposite to the spigot body and the spigot body and the spigot extension cooperatively define a spigot lumen. The tubing includes an outer surface and a tubing lumen, wherein a coupling portion of the tubing is disposed around the spigot extension, permitting fluid communication between the tubing lumen and the spigot lumen. The collar is disposed radially around the outer surface of the tubing and axially between the flared portion and the spigot body, wherein the collar radially engages the coupling portion of the tubing disposed around the spigot extension to axially and radially retain the tubing with the spigot.

6 Claims, 9 Drawing Sheets

(56) References Cited

U.S. PATENT DOCUMENTS

| | | | |
|---|---|---|---|
| 8,091,928 B2* | 1/2012 | Carrier | F16L 33/02 285/242 |
| 2003/0140462 A1 | 7/2003 | Yuzuriha et al. | |
| 2004/0146341 A1 | 7/2004 | Sundheimer et al. | |
| 2006/0127165 A1 | 6/2006 | Vasek et al. | |
| 2008/0197624 A1* | 8/2008 | Nakano | F16L 33/34 285/226 |
| 2008/0309082 A1* | 12/2008 | Bonetto | F16L 33/2071 285/369 |
| 2010/0084860 A1* | 4/2010 | Cariccia | F16L 33/2076 285/256 |
| 2016/0363247 A1* | 12/2016 | McCure | F16L 37/0985 |
| 2017/0138518 A1* | 5/2017 | Blake | F16L 33/2071 |

\* cited by examiner

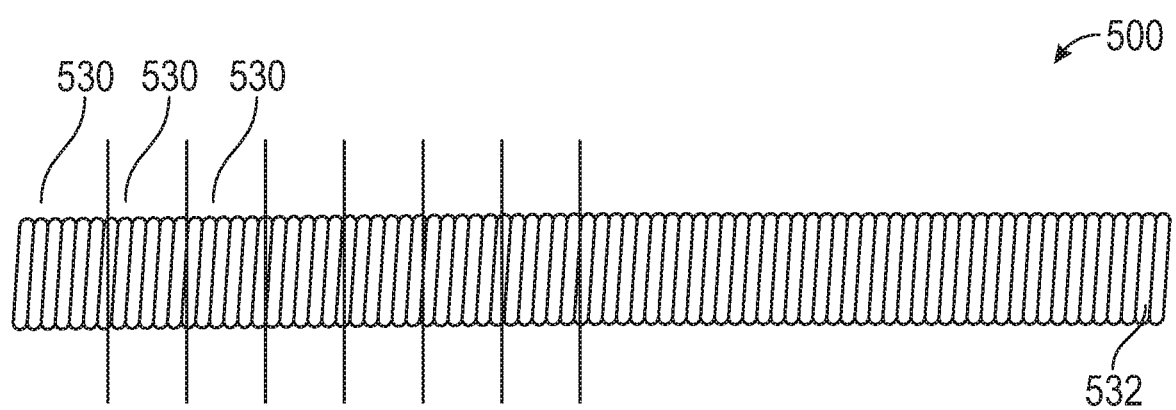
FIG. 10
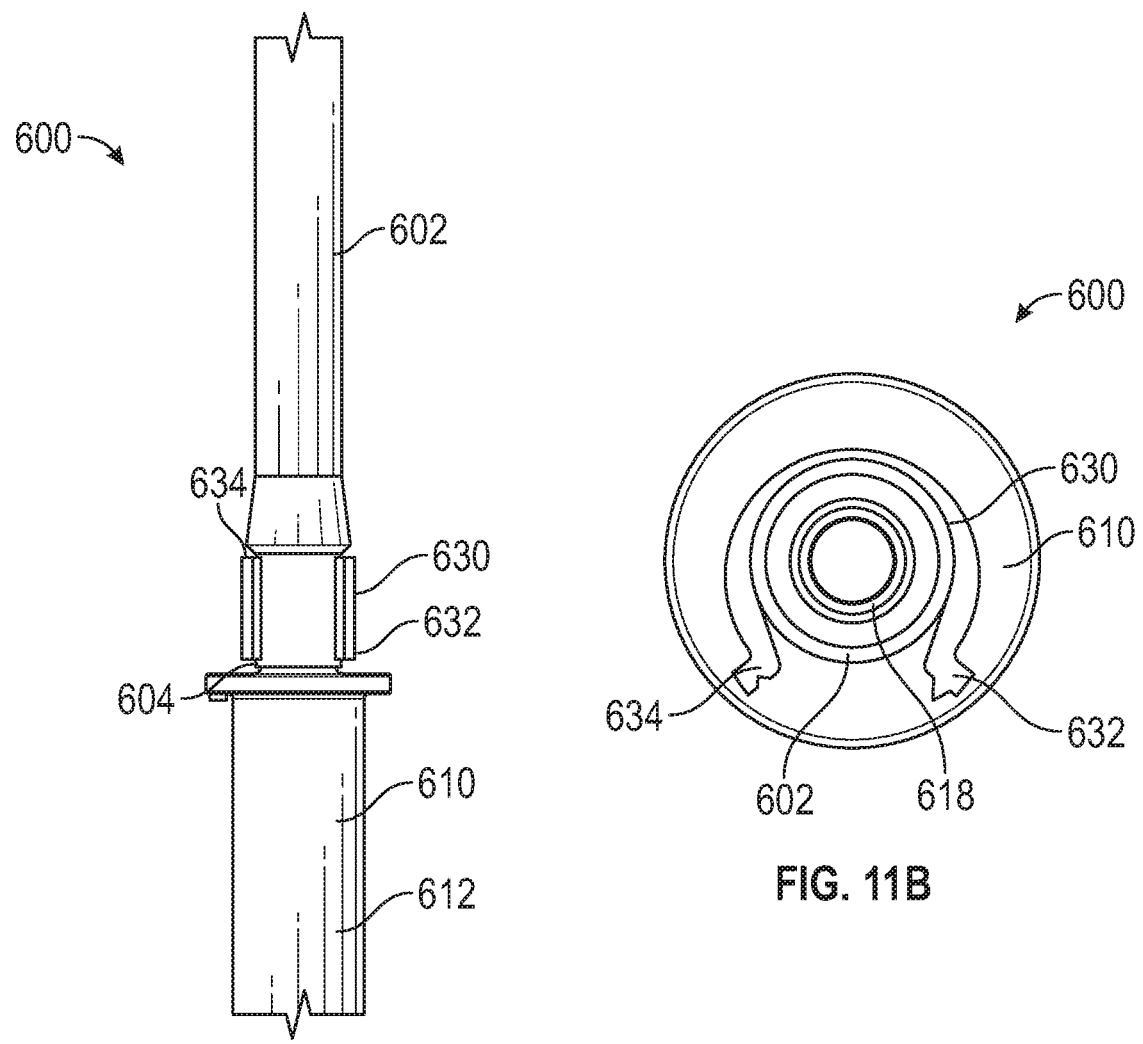
FIG. 11A
FIG. 11B

TUBING RETENTION DEVICE

FIELD OF THE INVENTION

The present disclosure generally relates to devices to facilitate the coupling of tubing, and, in particular, devices to facilitate the coupling of tubing to a spigot.

BACKGROUND

Medical treatments often include the infusion of a medical fluid (e.g., a saline solution, a liquid medication, lipids, blood products, etc.) to patients from a source of fluid, for example, an IV bag or other medical fluid containers. Medical fluids are often transferred between devices or to the patient by tubing. The tubing can be sealingly engaged to a device or container at a spigot.

During operation, the tubing may lose sealing engagement with the spigot or may become dislodged from the spigot.

In some applications, the tubing may leak or air may be introduced into the tubing, disrupting the medical treatment.

SUMMARY

In some applications, a tubing and spigot interface may lose sealing engagement or become dislodged. However, many tubing coupling configurations may not effectively resist axial forces, may damage the tubing, or may be cumbersome to assemble.

Therefore, in some applications, certain tubing coupling configurations may not reliably secure the tubing to the spigot.

The disclosed subject matter relates to tubing retention systems. In certain embodiments, a tubing retention is disclosed that comprises a spigot comprising: a spigot body; and a spigot extension extending from the spigot body, wherein the spigot extension comprises a flared portion opposite to the spigot body and the spigot body and the spigot extension cooperatively define a spigot lumen; a tubing comprising: an outer surface; and a tubing lumen, wherein a coupling portion of the tubing is disposed around the spigot extension, permitting fluid communication between the tubing lumen and the spigot lumen; and a collar disposed radially around the outer surface of the tubing and axially between the flared portion and the spigot body, wherein the collar radially engages the coupling portion of the tubing disposed around the spigot extension to axially and radially retain the tubing with the spigot.

In certain embodiments, a method comprises disposing a collar around an outer surface of a tubing; advancing a coupling portion of the tubing around a spigot extension of a spigot; advancing the collar toward the coupling portion of the tubing around the spigot extension; melting a portion of the collar to radially engage the coupling portion of the tubing around the spigot extension; and axially and radially retaining the tubing with the spigot via the collar.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 10 is an elevation view of a collar stock, in accordance with various aspects of the present disclosure.

FIG. 11A is an elevation view of a tubing retention system, in accordance with various aspects of the present disclosure.

FIG. 11B is a plan view of the tubing retention system of FIG. 11A.

DETAILED DESCRIPTION

Figure 2A:
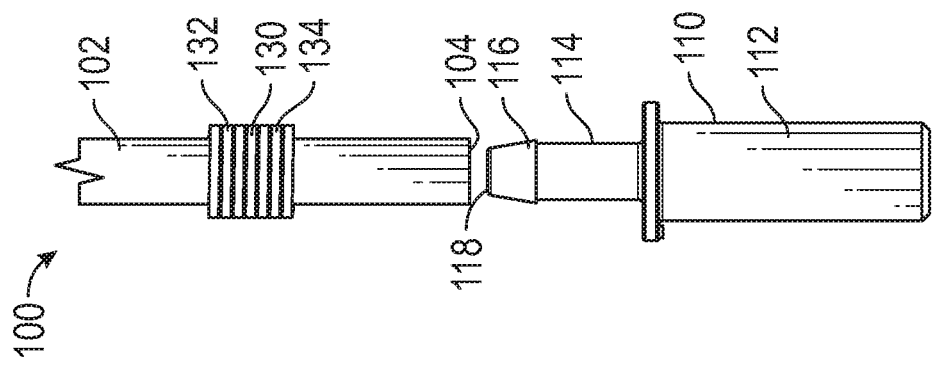
FIG. 2A is an elevation view of the tubing retention system of FIG. 1A, prior to coupling the tubing to the spigot.

The disclosed tubing retention system incorporates a collar to radially engage the coupling portion of the tubing. Prior to securing the tubing, the collar can expand and contract to be freely moved along the outer surface of the tubing. After positioning, the collar can be secured to engage and retain the tubing to the spigot. By allowing the collar to expand and contract, the collar can be positioned without damaging the tubing. Further, by securing the collar in the desired position, the collar can reliably and securely couple the tubing to the spigot.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical or similar element numbers for ease of understanding. Reference numbers may have letter suffixes appended to indicate separate instances of a common element while being referred to generically by the same number without a suffix letter.

While the following description is directed to securing tubing to a spigot, it is to be understood that this description is only an example of usage and does not limit the scope of the claims. Various aspects of the disclosed tubing retention systems may be used in any application where it is desirable to secure tubing.

The disclosed tubing retention system overcomes several challenges discovered with respect to certain conventional tubing retention systems. One challenge with certain conventional tubing retention systems is that conventional collars may be relatively rigid during positioning and therefore may require high amounts of force to position the collar over desired portions of the tubing. Further, certain conventional tubing retention systems may utilize solvent or other adhesives, which may require specialized procedures or handling. Because conventional tubing retention systems may damage tubing during assembly, have low joint strength, may require special handling due to volatility and/or flammability, occlude flow paths, may be difficult to inspect, and may require significant time before joint strength is realized, the use of conventional tubing retention systems is undesirable.

Therefore, in accordance with the present disclosure, it is advantageous to provide tubing retention systems as described herein that allow secure coupling of tubing to the spigot, without damaging tubing or requiring special handling.

An example of a tubing retention system that effectively secures tubing to the spigot is now described.

Figure 1B:
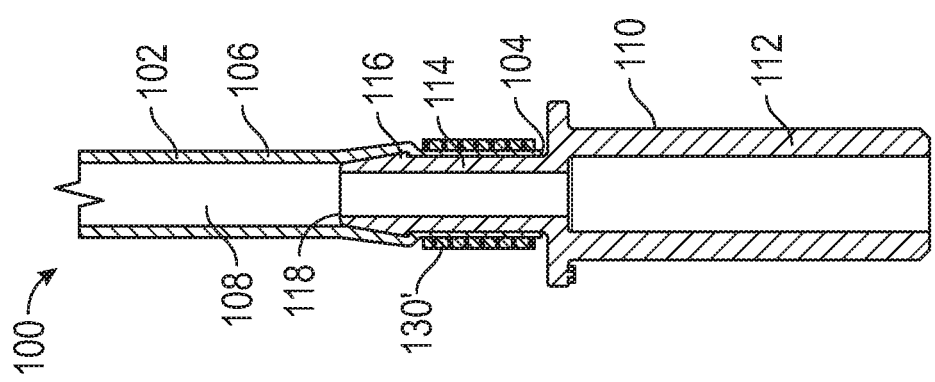
FIG. 1B is a cross-sectional view of the tubing retention system of FIG. 1A.
Figure 1A:
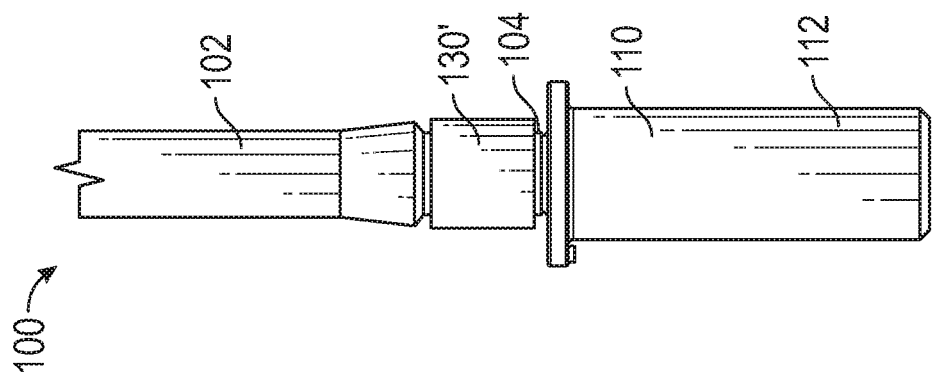
FIG. 1A is an elevation view of a tubing retention system, in accordance with various aspects of the present disclosure.

FIG. 1A is an elevation view of a tubing retention system 100, in accordance with various aspects of the present disclosure. FIG. 1B is a cross-sectional view of the tubing retention system 100 of FIG. 1A. With reference to FIGS. 1A and 1B, the tubing retention system 100 securely retains the tubing 102 to the spigot 110 to allow for reliable transfer of medical fluid therethrough.

In the depicted example, the coupling portion 104 of the tubing 102 is disposed over the spigot extension 114 of the spigot 110. By disposing the coupling portion 104 over the spigot extension 114, the tubing lumen 108 is in fluid communication with the spigot lumen 118, facilitating fluid flow between the tubing 102 and the spigot 110. In some embodiments, the spigot lumen 118 allows fluid flow from the spigot extension 114 into the spigot body 112.

As described herein, an engaged collar 130' can be positioned and engaged around the coupling portion 104 to retain the tubing 102 to the spigot 110. In the depicted example, the engaged collar 130' radially engages the outer surface 106 of the tubing 102 to radially compress the coupling portion 104 against spigot extension 114. By radially compressing the coupling portion 104 against the spigot extension 114, the amount of axial or pullout force required to overcome the frictional force between the coupling portion 104 and the spigot extension 114 is increased.

Additionally, the engaged collar 130' can constrain the radial expansion of the tubing 102 to prevent the tubing 102 from moving relative to the barbed or flared portion 116 of the spigot extension 114. As illustrated, the flared portion 116 of the spigot extension 114 can have an increased radius or diameter relative to the remainder of the spigot extension 114. In some embodiments, the flared portion 116 can have a diameter that is larger than the resting or nominal diameter of the tubing lumen 108, requiring the tubing 102 to stretch to allow the tubing 102 to be positioned over the flared portion 116 of the spigot extension 114. As can be appreciated, by radially stretching the tubing 102 over the flared portion 116 and effectively creating a compressive force against the flared portion 116, the pullout force required to overcome the frictional force between flared portion 116 and the tubing 102 is increased.

As described herein, the tubing 102 can be formed from a resilient material that returns to the nominal, or other smaller diameter when disposed around the spigot extension 114 after passing the flared portion 116.

As described herein, the engaged collar 130' maintains a generally fixed diameter, constraining the coupling portion 104 or otherwise preventing the radial expansion of the coupling portion 104. In some embodiments, the engaged collar 130' constrains the diameter of the tubing lumen 108 to a diameter that is smaller than the diameter of the flared portion 116. As described herein, the engaged collar 130' can provide a compressive force against the coupling portion 104. By preventing the radial expansion of the coupling portion 104, the engaged collar 130' prevents the coupling portion 104, or the tubing 102 generally, from moving past the flared portion 116 of the spigot extension 114. As can be appreciated, the engaged collar 130' can be frictionally engaged with the outer surface 106 of the tubing 102, preventing axial movement or displacement of the engaged collar 130'.

Advantageously, the use of the engaged collar 130' in conjunction with the flared portion 116 significantly increases the amount of pullout force needed to dislodge the tubing 102 from the spigot 110.

As can be appreciated, the tubing retention system 100 can facilitate the assembly of the fluid connection between the tubing 102 and the spigot 110. As discussed herein, the tubing 102 comprise an expandable and/or elastomeric material to allow the tubing lumen 108 to be positioned over the spigot extension 114, including the flared portion 116 of the spigot extension 114. Further, prior to engagement, a collar can comprise an expandable and/or elastomeric material and/or construction to allow the collar to be positioned along the length of the tubing 102, including portions of the tubing 102 disposed over the flared portion 116 of the spigot extension 114. As described herein, once positioned, the collar can be melted, unified or otherwise engaged to form the engaged collar 130' configured to engage and/or radially constrain the tubing 102.

Figure 2B:
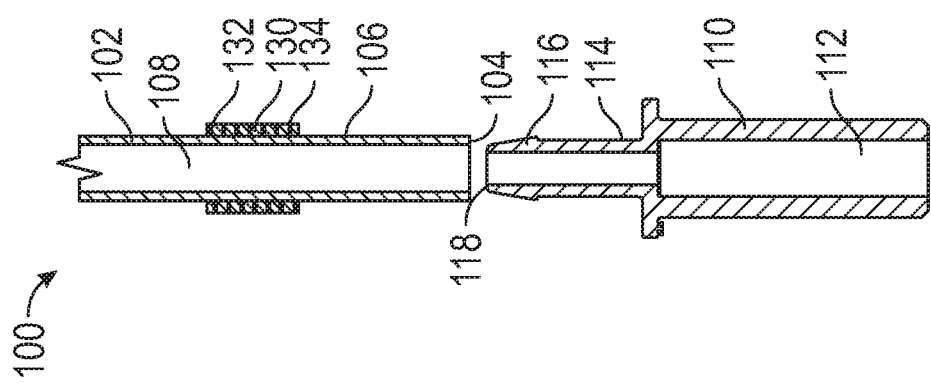
FIG. 2B is a cross-sectional view of the tubing retention system of FIG. 2A.

FIG. 2A is an elevation view of the tubing retention system 100 of FIG. 1A, prior to coupling the tubing 102 to the spigot 110. FIG. 2B is a cross-sectional view of the tubing retention system 100 of FIG. 2A. With reference to FIGS. 2A and 2B, prior to positioning the tubing 102 over the spigot extension 114, a collar 130 can be positioned over the outer surface 106 of the tubing 102.

As can be appreciated, prior to engagement, the collar 130 is radially and/or axially expandable to allow the collar 130 to be positioned along the tubing 102 with low friction and resistance. In the depicted example, the collar 130 can be formed from a collar body 132 have a generally wire-like or filament structure. Optionally, the cross-sectional profile of the filament structure of the collar body 132 can be circular, rounded, rectangular, or any other suitable cross-sectional profile. As illustrated, the filament structure of the collar body 132 is generally wound in a helical or spiral manner and is configured to be disposed around the tubing 102. The winding of the collar body 132 can define voids 134 between the windings of the collar body 132 that can expand and contract to allow the collar 130 to expand and contract. Optionally, the collar body 132 can be formed from a suitable polymer material.

During positioning, the wound structure of the collar body 132 can expand and contract radially and/or axially with relatively low force to allow the collar 130 to be moved along uneven surfaces of the tubing 102. Advantageously, by allowing the collar 130 to expand and contract, the underlying tubing 102 can be less susceptible to tearing or other damage.

Figure 3B:
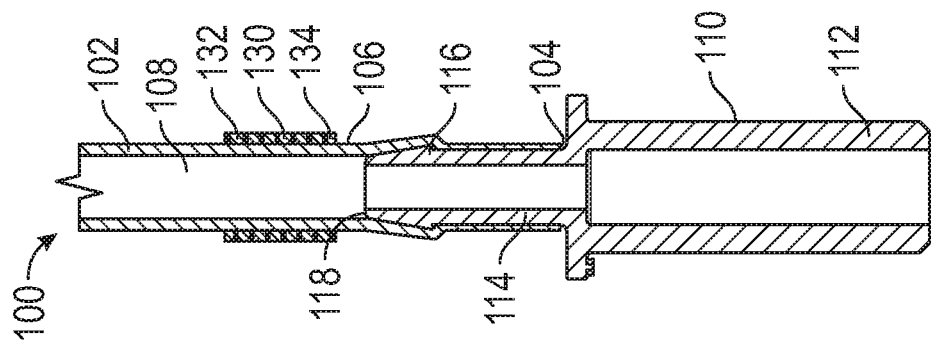
FIG. 3B is a cross-sectional view of the tubing retention system of FIG. 3A.
Figure 3A:
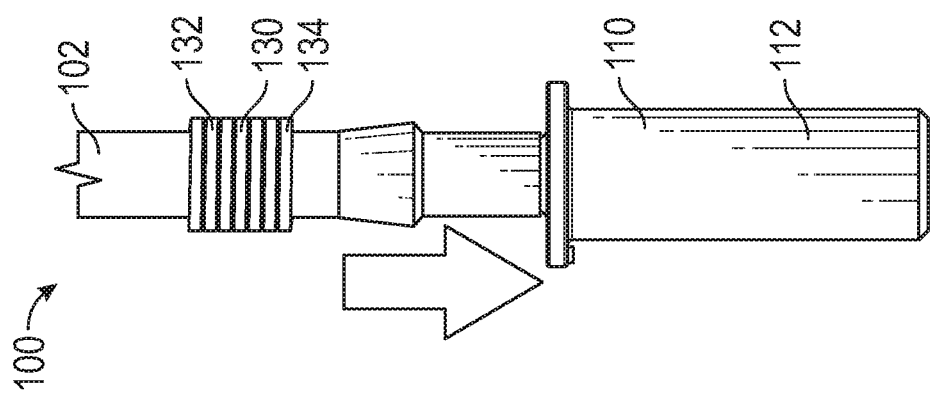
FIG. 3A is an elevation view of the tubing retention system of FIG. 1A, with the tubing coupled to the spigot.

FIG. 3A is an elevation view of the tubing retention system 100 of FIG. 1A, with the tubing 102 coupled to the spigot 110. FIG. 3B is a cross-sectional view of the tubing retention system 100 of FIG. 3A. With reference to FIGS. 3A and 3B, the coupling portion 104 of the tubing 102 is positioned over the spigot extension 114 of the spigot 110. The tubing 102 can be urged toward the spigot 110 until the coupling portion 104 is past the flared portion 116 of the spigot 110 and may contact the spigot body 112.

In some embodiments, the outer diameter of the spigot extension 114 along with the flared portion 116 of the spigot extension 114 can be larger than the inner diameter of the tubing lumen 108. Optionally, the outer diameter of the spigot extension 114 can be the same or similar to the inner diameter of the tubing lumen 108. As described herein, the tubing 102 can expand to allow the tubing lumen 108 to be positioned over the spigot extension 114 and the flared portion 116. As can be appreciated, by radially stretching or expanding the tubing 102 over the spigot extension 114 and/or the flared portion 116 and effectively creating a compressive force therebetween, the pullout force required to overcome the frictional force between the spigot extension 114 and/or the flared portion 116 and the tubing 102 is increased.

Figure 4C:
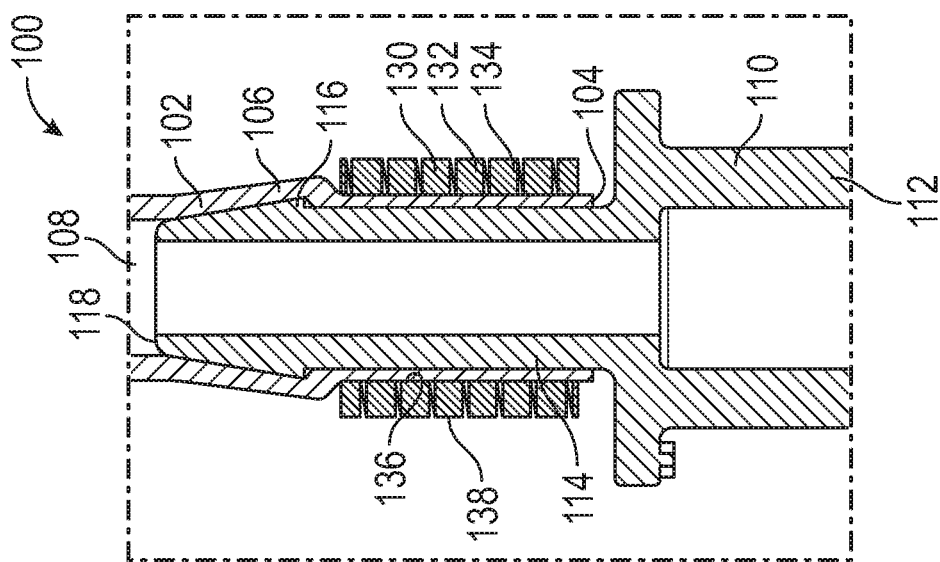
FIG. 4C is a detail cross-sectional view of the collar of FIG. 4A.
Figure 4B:
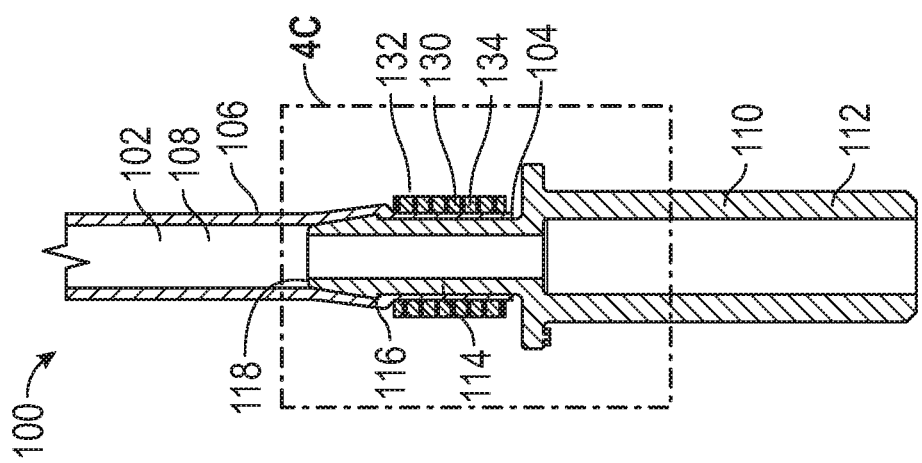
FIG. 4B is a cross-sectional view of the tubing retention system of FIG. 4A.
Figure 4A:
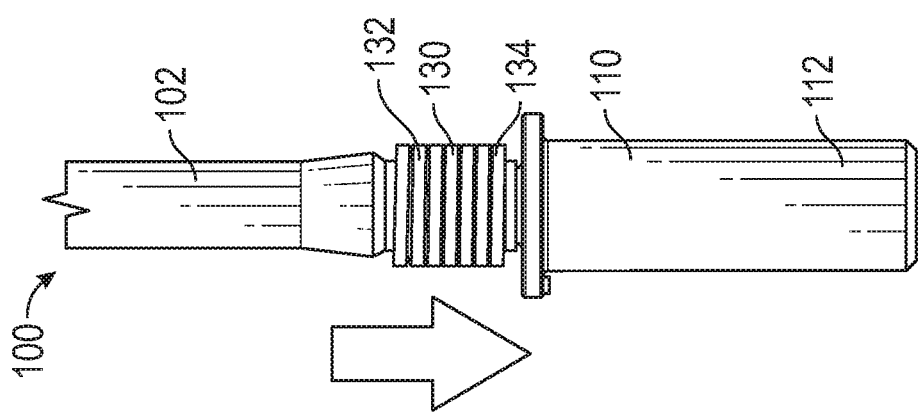
FIG. 4A is an elevation view of the tubing retention system of FIG. 1A, with the collar disposed around the coupling portion of the tubing.

FIG. 4A is an elevation view of the tubing retention system 100 of FIG. 1A, with the collar 130 disposed around the coupling portion 104 of the tubing 102. FIG. 4B is a cross-sectional view of the tubing retention system 100 of FIG. 4A. FIG. 4C is a detail cross-sectional view of the collar 130 of FIG. 4A. With reference to FIGS. 4A-4C, the collar 130 is positioned over the coupling portion 104 of the tubing 102. As can be appreciated, the construction of the collar body 132 can allow the collar 130 to radially expand and pass over the tubing 102 disposed over the flared portion 116 of the spigot 110. In some embodiments, the collar 130 can be configured to extend the axial length of the coupling portion 104 between the spigot body 112 and the flared portion 116.

Prior to the engagement of the collar 130 over the coupling portion 104, the voids 134 of the collar 130 are free to expand and contract, allowing the collar 130 to expand and contract. As illustrated, prior to engagement, the inner diameter 136 and the outer diameter 138 of the collar 130 are unfused or separated to allow the voids 134 to expand and contract as needed.

Figure 5C:
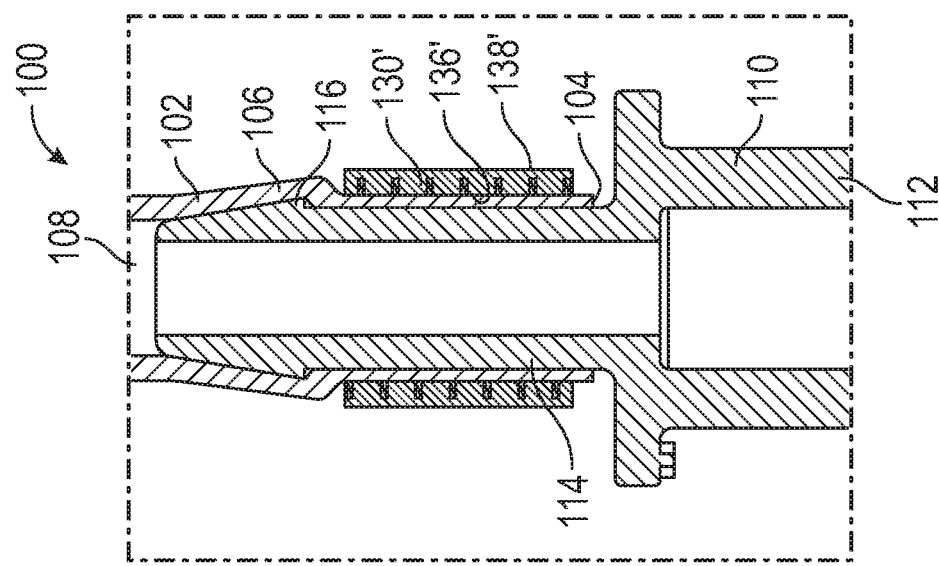
FIG. 5C is a detail cross-sectional view of the collar of FIG. 5A.
Figure 5B:
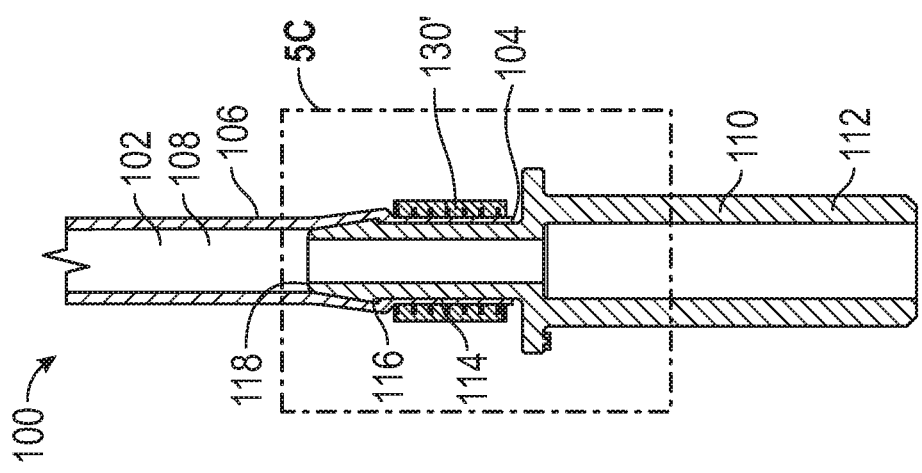
FIG. 5B is a cross-sectional view of the tubing retention system of FIG. 5A.
Figure 5A:
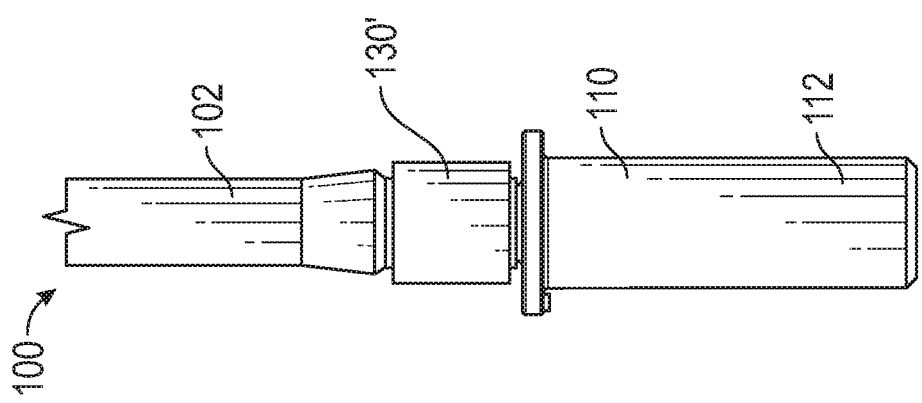
FIG. 5A is an elevation view of the tubing retention system of FIG. 1A, with the collar secured around the coupling portion of the tubing.

FIG. 5A is an elevation view of the tubing retention system 100 of FIG. 1A, with the collar 130' secured around the coupling portion 104 of the tubing 102. FIG. 5B is a cross-sectional view of the tubing retention system 100 of FIG. 5A. FIG. 5C is a detail cross-sectional view of the collar 130' of FIG. 5A. With reference to FIGS. 5A-5C, after the collar 130 is positioned over the coupling portion 104 as described with respect to FIGS. 4A-4C, the collar 130 can be engaged to retain the tubing 102 with the spigot 110. As illustrated, the rigid or engaged collar 130' radially engages the outer surface 106 of the tubing 102 to radially compress the coupling portion 104 against the spigot extension 114. Further, the engaged collar 130' can constrain the radial expansion of the tubing 102 to prevent the tubing 102 from moving relative to the flared portion 116 of the spigot extension 114.

In the depicted example, the material of the engaged collar 130' is melted or otherwise unified to form the engaged collar 130'. In some embodiments, the outer diameter 138' of the engaged collar 130' is melted or otherwise unified to eliminate the voids 134 that previously permitted expansion of the collar 130. Optionally, by unifying the engaged collar 130' the inner diameter 136' can form a ridged friction surface to engage against the outer surface 106 of the tubing 102, enhancing the engagement between the engaged collar 130' and the tubing 102.

Figure 6B:
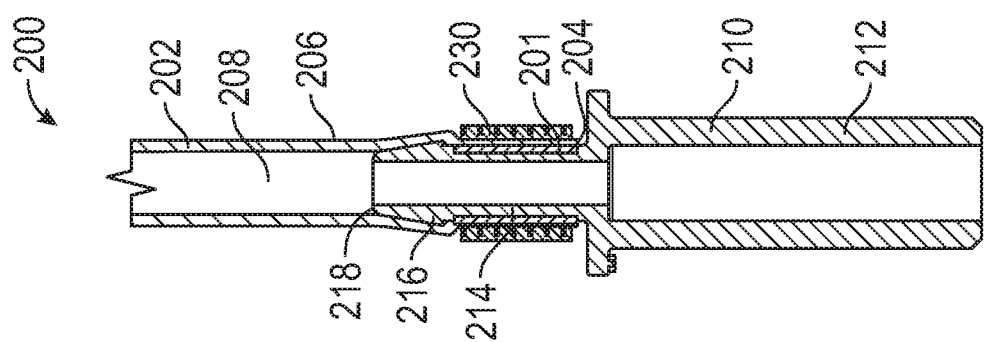
FIG. 6B is a cross-sectional view of the tubing retention system of FIG. 6A with the collar secured around the coupling portion of the tubing.
Figure 6A:
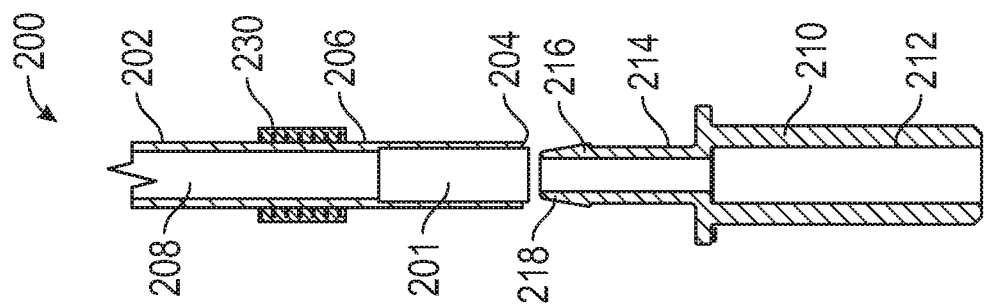
FIG. 6A is a cross-sectional view of a tubing retention system, in accordance with various aspects of the present disclosure.

FIG. 6A is a cross-sectional view of a tubing retention system 200, in accordance with various aspects of the present disclosure. In the depicted example, the tubing 202 can include a solvent 201. As illustrated, prior to coupling, the solvent 201 can be applied to the tubing lumen 208. The solvent 201 can be disposed at or near the coupling portion 204 of the tubing 202. In some embodiments, the solvent 201 can aid in bonding and retaining the tubing 202 to the spigot 210. As can be appreciated, the solvent 201 can serve as a lubricant to allow the tubing 202 to pass over the spigot extension 214 with reduced friction.

FIG. 6B is a cross-sectional view of the tubing retention system 200 of FIG. 6A with the collar 230 secured around the coupling portion 204 of the tubing 202. After coupling the tubing 202 with the spigot 210, the solvent 201 can be cured to enhance the retention between the tubing 202 and the spigot 210. Advantageously, the collar 230 can retain the tubing 202 while the solvent 201 cures, providing immediate joint strength. Further, upon curing the solvent 201 can provide supplemental joint strength, in addition to the joint strength provided by the collar 230.

Figure 7A:
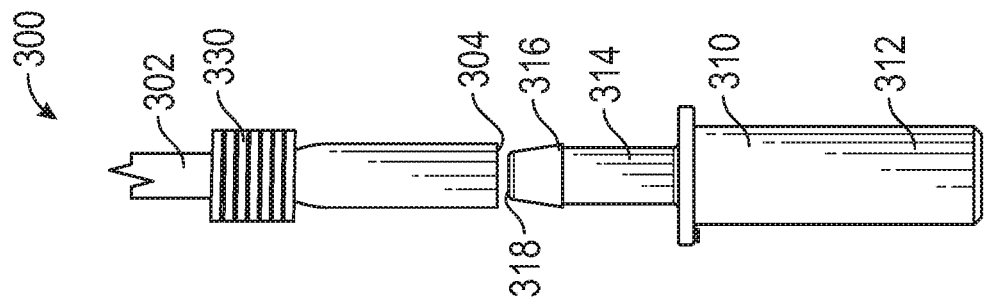
FIG. 7A is an elevation view of a tubing retention system, in accordance with various aspects of the present disclosure.
Figure 7B:
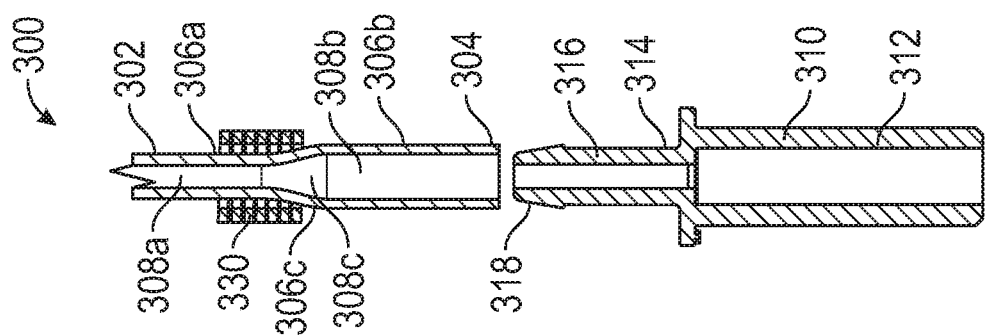
FIG. 7B is a cross-sectional view of the tubing retention system of FIG. 7A.

FIG. 7A is an elevation view of a tubing retention system 300, in accordance with various aspects of the present disclosure. FIG. 7B is a cross-sectional view of the tubing retention system 300 of FIG. 7A. With reference to FIGS. 7A and 7B, in some embodiments, the tubing 302 can flare or increase in size or diameter. For example, the tubing 302 can include a tubing lumen 308a that flares or increases in diameter to a larger tubing lumen 308b at or near the coupling portion 304 of the tubing. As can be appreciated, the tubing lumen 308a can be used to maintain desired flow characteristics, while tubing lumen 308b can facilitate a connection with the spigot 310. Optionally, the tubing lumen 308a can be a microbore tubing. Optionally, the tubing lumen 308a transitions to the larger diameter tubing lumen 308b at a tubing lumen transition 308c.

In some embodiments, the tubing 302 can include an outer surface 306a that flares or increases in diameter to a larger outer surface 306b diameter to accommodate the larger tubing lumen 308b. Optionally, the outer surface 306a transitions to the larger outer surface 306b diameter at an outer surface transition 306c. As can be appreciated, the collar 330 can radially expand to pass over the various diameters of the outer surface 306a, the outer surface 306b, and/or the outer surface transition 306c.

Figure 8B:
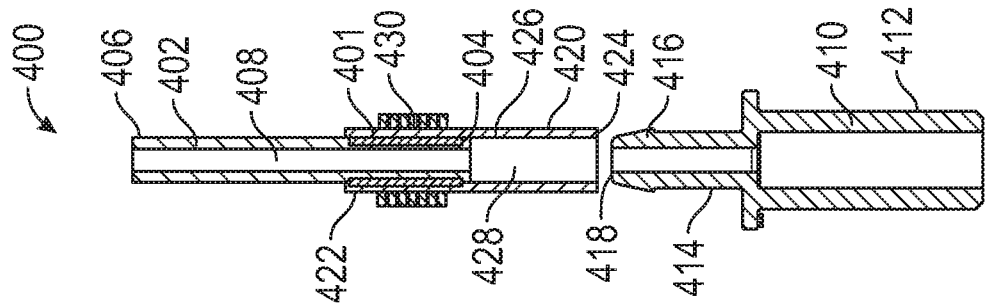
FIG. 8B is a cross-sectional view of the tubing retention system of FIG. 8A.
Figure 8A:
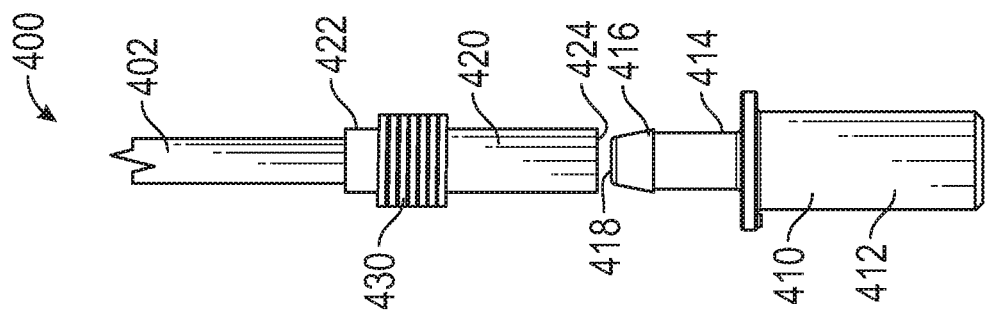
FIG. 8A is an elevation view of a tubing retention system, in accordance with various aspects of the present disclosure.

FIG. 8A is an elevation view of a tubing retention system 400, in accordance with various aspects of the present disclosure. FIG. 8B is a cross-sectional view of the tubing retention system 400 of FIG. 8A. With reference to FIGS. 8A and 8B, in some embodiments, the tubing retention system 400 can be used with tubing 402 that may not be positioned, or is not desirable to position over the spigot extension 414. For example, the tubing 402 may be microbore tubing that may not sufficiently expand or stretch to be positioned over the spigot extension 414.

Optionally, the tubing 402 can include an expander or tubing coupler 420 that couples to the tubing 402 and facilitates a connection between the tubing 402 and the spigot 410. In the depicted example, the tubing coupler 420 is coupled to the outer surface 406 of the tubing 402. Optionally, the tubing coupler 420 can be coupled to the tubing 402 with solvent 401. Solvent 401 can be applied to an upper portion of a coupler lumen 428 of the tubing coupler 420. The solvent 401 can be cured to bond the tubing 402 and the tubing coupler 420.

Figure 9A:
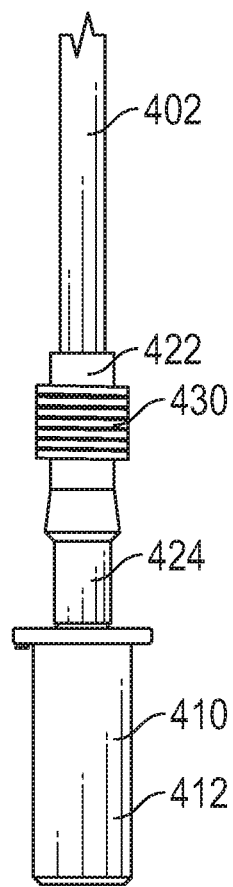
FIG. 9A is an elevation view of the tubing retention system of FIG. 8A, with the tubing coupled to the spigot.
Figure 9B:
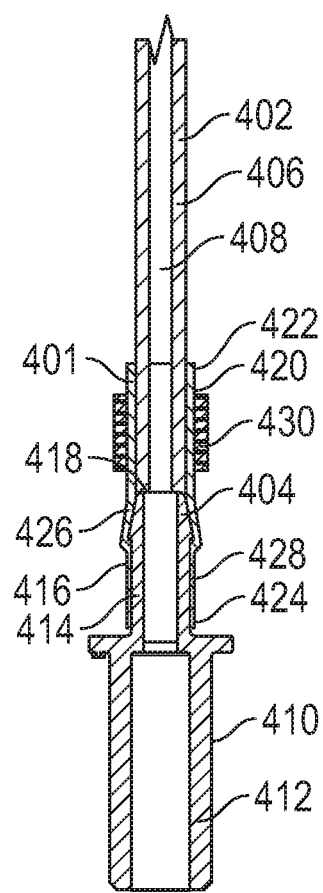
FIG. 9B is a cross-sectional view of the tubing retention system of FIG. 9A.

FIG. 9A is an elevation view of the tubing retention system 400 of FIG. 8A, with the tubing 402 coupled to the spigot 410. FIG. 9B is a cross-sectional view of the tubing retention system 400 of FIG. 9A. After coupling the tubing coupler 420 to the tubing 402, the tubing coupler 420 can be disposed over the spigot extension 414. As can be appreciated, the tubing coupler 420 can expand to be positioned over the spigot extension 414 and the flared portion 416 as described herein with respect to tubing 102. In some embodiments, the end 404 of the tubing 402 may abut against the spigot extension 414.

During positioning, the collar 430 can be moved over the tubing 402 and/or the tubing coupler 420 to be disposed at the coupling portion 424 of the tubing coupler 420. The collar 430 can radially expand to pass over the outer surface 406 of the tubing 402 and the outer surface 426 of the tubing coupler 420, including the portion of the tubing coupler 420 that is disposed over the flared portion 416 of the spigot 410.

FIG. 10 is an elevation view of a collar stock 500, in accordance with various aspects of the present disclosure. In the depicted example, collars 530 can be formed by cutting or otherwise separating portions from the collar stock 500. In some embodiments, the collar stock 500 can be formed by first extruding the collar body 532 and then winding the collar body 532 around a mandrel to form a cylindrical shape. As can be appreciated, the collar body 532 can be wound in a spiral-like or helical pattern. As can be appreciated, the collar body 532 can be formed by molding or any other suitable process.

FIG. 11A is an elevation view of a tubing retention system 600, in accordance with various aspects of the present disclosure. FIG. 11B is a plan view of the tubing retention system 600 of FIG. 11A. With reference to FIGS. 11A and 11B, the tubing retention system 600 can utilize a hinged or otherwise closable collar 630 to retain the tubing 602 with the spigot 610. As illustrated, prior to engagement, the collar 630 can generally radially expand by opening or expanding about a hinged portion of the collar 630 to allow the collar 630 to be positioned along the tubing 602 with low friction and resistance. In the depicted example, a space between the ends 631 and 634 of the collar 630 can be radially and/or circumferentially expanded or contracted to allow the collar 630 to expand and/or contract. The collar 630 can include a hinged portion radially opposite to the ends 631 and 634.

Figure 12A:
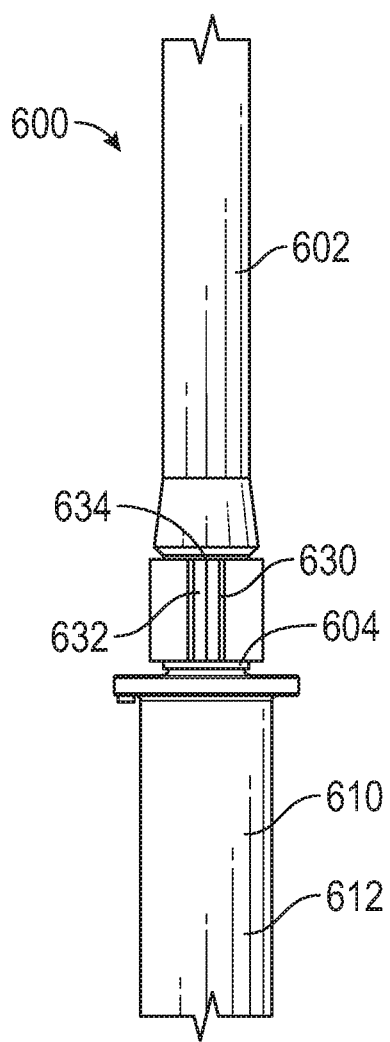
FIG. 12A is an elevation view of the tubing retention system of FIG. 11A with the collar secured around the coupling portion of the tubing.
Figure 12B:
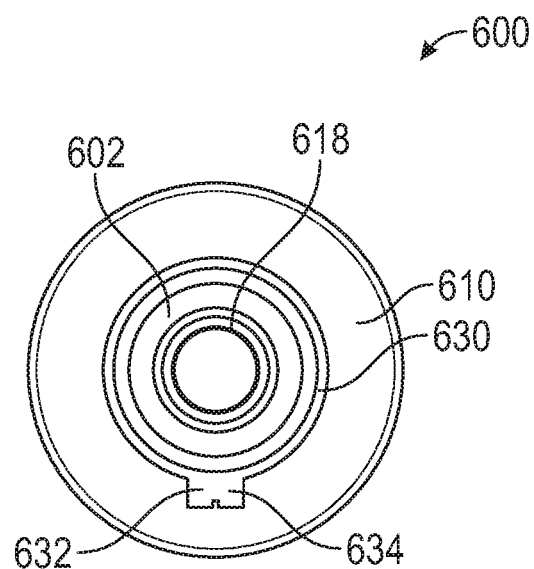
FIG. 12B is a plan view of the tubing retention system of FIG. 12A.

FIG. 12A is an elevation view of the tubing retention system 600 of FIG. 11A with the collar 630 secured around the coupling portion 604 of the tubing 602. FIG. 12B is a plan view of the tubing retention system 600 of FIG. 12A. With reference to FIGS. 12A and 12B, after the collar 630 is positioned over the coupling portion 604, the collar 630 can be engaged to retain the tubing 602 with the spigot 610. In the depicted example, the ends 631 and 634 can be radially and/or circumferentially positioned together or otherwise closed to engage the collar 630 with the tubing 102. The ends 631 and 634 of the collar 630 can be engaged together by a friction, interference, or snap fit. The ends 631 and 634 can be melted, ultrasonically welded, or bonded to join the ends 631 and 634 of the collar 630 together.

Figure 13:
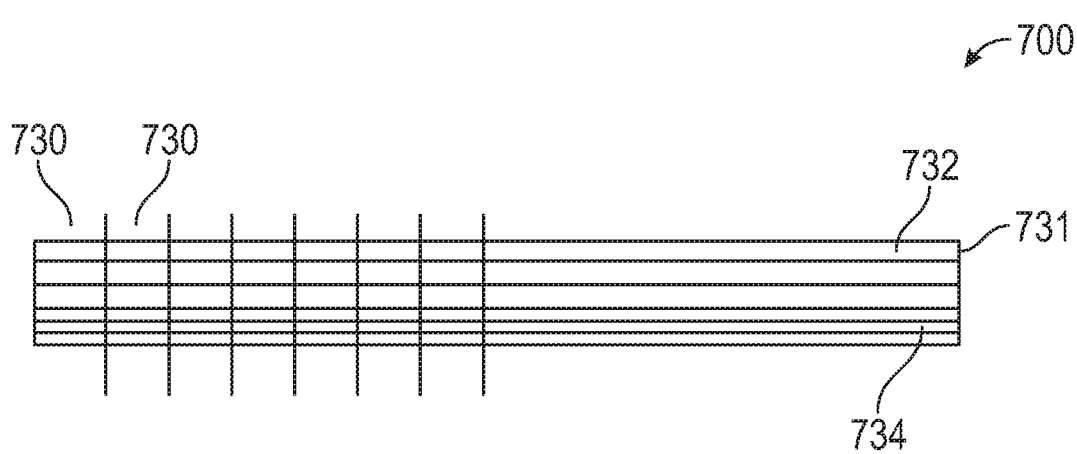
FIG. 13 is an elevation view of a collar stock, in accordance with various aspects of the present disclosure.

FIG. 13 is an elevation view of a collar stock 700 in accordance with various aspects of the present disclosure. In the depicted example, collars 730 can be formed by cutting or otherwise separating portions from the collar stock 700. In some embodiments, the collar stock 700 can be formed by extruding the collar body 732. As can be appreciated, the collar body 732 can be formed by molding or any other suitable process.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A tubing retention system comprising:
   a spigot comprising:
      a spigot body; and
      a spigot extension extending from the spigot body, wherein:
         the spigot extension comprises a flared portion opposite to the spigot body, and
         the spigot body and the spigot extension cooperatively define a spigot lumen;
   a tubing comprising:
      an outer surface; and
      a tubing lumen, wherein a coupling portion of the tubing is disposed around the spigot extension, permitting fluid communication between the tubing lumen and the spigot lumen; and
   a collar comprising a helical body wound radially around the outer surface of the tubing and axially between the flared portion and the spigot body, wherein in an expandable configuration, the helical body defines a plurality of voids configured expand and contract, permitting the helical body to radially expand and contract, and in an unified configuration the helical body is fused to unify the plurality of voids, preventing the helical body from radially expanding and contracting, permitting the helical body to radially engage the coupling portion of the tubing disposed around the spigot extension to axially and radially retain the tubing with the spigot.

2. The tubing retention system of claim 1, wherein the coupling portion of the tubing comprises a coupling inner diameter equal to or larger than a spigot extension outer diameter.

3. The tubing retention system of claim 2, wherein the tubing lumen flares from a tubing lumen inner diameter to the coupling inner diameter.

4. The tubing retention system of claim 2, wherein the coupling portion of the tubing comprises an expander sleeve coupled to the tubing.

5. The tubing retention system of claim 1, wherein the collar comprises a meltable polymer material, wherein melting the collar unifies the plurality of voids.

6. The tubing retention system of claim 1, wherein the collar extends along a length of the spigot extension and terminates before the flared portion.

* * * * *